United States Patent [19]
Powell et al.

[11] Patent Number: 5,502,559
[45] Date of Patent: Mar. 26, 1996

[54] APPARATUS AND METHOD FOR DETECTION OF MATERIAL USED IN CONSTRUCTION OF CONTAINERS AND COLOR OF SAME

[75] Inventors: Ken R. Powell, Centreville; Rusty Driscoll, Leesburg, both of Va.

[73] Assignee: Environmental Products Corporation, Fairfax, Va.

[21] Appl. No.: 350,739

[22] Filed: Dec. 7, 1994

Related U.S. Application Data

[63] Continuation of Ser. No. 144,030, Nov. 1, 1993, abandoned.

[51] Int. Cl.$^6$ .............................. G01N 21/00; B07C 5/00
[52] U.S. Cl. .................. 356/73; 250/223 B; 209/524; 209/580; 209/588; 209/582; 209/577
[58] Field of Search ..................... 356/73; 250/223 B; 209/524, 576–577, 580–582, 588

[56] References Cited

U.S. PATENT DOCUMENTS

| | | | |
|---|---|---|---|
| 4,076,979 | 2/1978 | Walter et al. | 250/226 |
| 4,120,591 | 10/1978 | van Valkenburg . | |
| 4,482,250 | 11/1984 | Hirvonen et al. | 356/369 |
| 4,558,786 | 12/1985 | Lane . | |
| 4,919,534 | 4/1990 | Reed | 250/223 B |
| 5,150,307 | 9/1992 | McCourt et al. | 356/73 |
| 5,314,072 | 5/1994 | Frankel et al. | 209/524 |

FOREIGN PATENT DOCUMENTS

| | | | |
|---|---|---|---|
| 8806095 | 7/1988 | Germany . | |
| 3935334 | 4/1991 | Germany | 209/524 |

*Primary Examiner*—Frank Gonzalez
*Assistant Examiner*—Jason D. Eisenberg
*Attorney, Agent, or Firm*—Finnegan, Henderson, Farabow, Garrett & Dunner

[57] ABSTRACT

An apparatus for analyzing the character of a translucent container including a light source for directing a beam of light along an optical axis through a container. A first optical analyzer is provided for analyzing the color of light passing through a container. The first optical analyzer includes one or more detectors for generating signals in response to light incident thereon. A first directing means directs one or more portions of the beam of light passing through the container toward the one or more detectors. Means are provide for determining the color of the container depending upon the relative magnitudes of the signals from the one or more detectors.

21 Claims, 9 Drawing Sheets

FIG. 9 ly used deposit containers and bottles. One signifi-
APPARATUS AND METHOD FOR DETECTION OF MATERIAL USED IN CONSTRUCTION OF CONTAINERS AND COLOR OF SAME This application is a continuation of application Ser. No. 08/144,030, filed Nov. 1, 1993, now abandoned.

BACKGROUND OF THE INVENTION

This invention relates to the characterization of containers, and, more particularly, to a process and apparatus for determining the material of construction and the color of translucent and partially translucent containers.

In recent years, non-deposit containers for beverages and other goods have become widely used because their cost has been less than the cost of recycling and/or cleaning for reuse previously used deposit containers and bottles. One significant result of the widespread use of non-deposit containers has been increased litter in public places.

To combat litter and increase the amount of material that is recycled, several states have now enacted mandatory "deposit laws" that require the use of containers upon which a deposit must be paid. When the customer purchases a product in such a container, a container deposit, typically one to five cents, is added to the purchase price. After consumption of the product, the consumer can obtain a refund of the deposit by returning the empty container for recycling. The amount of the deposit may be adjusted to create an incentive for returning the container that is greater than the inconvenience in doing so.

For the system of laws and incentives which require or encourage recycling to work properly, the scrap sales value of the recycled material must be sufficiently greater than the cost of recycling so that the recycling activity is profitable. Some materials which are candidates for recycling, such as aluminum, have an inherently high scrap value and have found widespread industry acceptance for recycling. Other scrap materials, for example glass and plastics such as polyethylene terephthalate (PET), have such a low scrap value that it is difficult for the value of the recycled material to exceed the costs of recycling.

One approach to improving the economics of recycling is to reduce its cost, particularly the cost of labor to receive containers and pay the proper refund. Some groups and individuals, such as retailers, have opposed mandatory deposit laws because, they argued, the high labor costs of processing recycled material makes recycling uneconomic, particularly for low scrap value materials, such as glass and PET. To reduce the labor costs, various machines that accept material for recycling and issue deposit refunds have been proposed, and some have been placed into service. Such machines do achieve their objective of reduced labor cost.

Another approach to improving the economics of recycling is to increase the scrap value of the recycled material. One method for increasing the scrap value is to segregate the returned material into groups, the value of which is greater compared to that of unsegregated material. For example, the value of glass and PET, per pound, is greater when the two have been segregated than when they are mixed together. Carrying the example further, the value of glass (or PET) that has been segregated by color (for example, clear, amber, or green) is greater than the value of glass that is mixed together.

In the past, the segregation of returned containers into classes has been labor intensive, so that the labor to perform the sorting may cost more than the increase in resale value of the segregated material. It would be highly desirable to provide a device that can perform the segregation of materials into such groups quickly and inexpensively, so that the cost of the sorting process is less than the enhancement in value obtained through sorting. It would be particularly desirable to provide such a sorting device that could be utilized at the point of return of the recycled material, because the person charged with recycling (typically the retailer) would enjoy the enhancement in profit arising from its use. It is expected that such an approach would greatly increase industry support for recycling glass and PET.

There are few available apparatuses and processes for grading and sorting containers by material of construction and color. U.S. Pat. No. 4,919,534 describes such an apparatus and process wherein polarized light of at least two wavelengths is passed through a container. Portions of the transmitted beam are analyzed by parallel and cross polarizers, the intensities of the analyzed beams are measured, and the sum and difference of the analyzed beams are determined to yield information concerning the color and composition of the container. While the apparatus and method of U.S. Pat. No. 4,919,534 proved useful in some applications, such as in a laboratory environment, the use of two wavelengths of light proved impractical in others, such as in an uncontrolled environment. Moreover, the apparatus and method of U.S. Pat. No. 4,919,534 proved to be "blind" to some colors of containers.

Apparatuses and processes for grading and sorting containers by material of construction and color should meet the requirements discussed previously, and also be operable with containers that are less than ideal, such as those which are dirty or have labels. The present invention fulfills this need, and further provides related advantages as will be apparent to those skilled in the art after reading this specification and the accompanying drawings.

SUMMARY OF THE INVENTION

The present invention provides an apparatus and process for automatically sorting translucent materials, that is, without the intervention or participation of a human being. Most commonly, the translucent materials being sorted are containers for beverages, comestible products, or the like and, among that group, most commonly beverage bottles. For the purpose of simplicity, but not to limit the scope of the present invention, the translucent materials being sorted in accordance with the present invention will be referred to simply as "containers."

Containers that are transparent or partially transparent may be sorted as between optically active and optically inactive materials, and as between different colors. As used herein the term "optically active" refers to materials that cause the rotation of polarized light. Some plastics, for example polyethylene terephthalate (PET) in the container industry, are optically active whereas glass, such as used in containers, is typically optically inactive.

The present invention provides an inexpensive, reliable method of sorting glass containers from PET containers, and any type of transparent or partially transparent container by color. The sorting is accomplished rapidly, normally as fast as a customer can place the containers into the apparatus. Once sorted, the containers are conveyed to bins for containers of the same color and composition.

In accordance with the present invention, an apparatus for analyzing the character of a translucent container is provided. The apparatus includes a light source for directing a beam of light along an axis through a container. A first optical analyzer for analyzing the color of light passing through the container is provided, including one or more detectors for generating signals in response to light incident thereon. First directing means direct one or more portions of the beam of light having passed through the container toward the one or more detectors. Determining means determine the color of the container depending upon the relative magnitudes of the signals from the one or more detectors.

Preferably, the apparatus of the present invention further comprises a second analyzer for determining if the container includes an optically active material. The second analyzer includes a polarizer disposed between the light source and the container support for polarizing light emanating from the light source in a first polarizing direction. A cross polarizer disposed along the axis intercepts light having passed through the container, the light having a second polarizing direction cross to the first polarizing direction. A polarization detector detects light passing through the cross polarizer and generates a polarization signal in proportion thereto. Determining means determine whether the container includes an optically active material depending upon the magnitude of the polarization signal.

An apparatus in accordance with the present invention may also include an intensity detector for detecting the intensity of light having passed through the container.

An apparatus in accordance with the present invention may embody directing means that include a first, second and third wavelength-specific beam splitters to direct light along a first, second and third sub-axis, respectively. Alternatively, the directing means may include a lens.

Thus, the apparatus and process of the invention provide an approach for accomplishing the sorting of containers that are at least partially transparent to light without the use of human labor or intervention. The approach is operable in conjunction with a recycling machine or the like, so that the customer is rewarded for recycling the material with a cash refund or coupons that may be redeemed. Other features and advantages of the present invention will be apparent from the following more detailed description of the invention, taken in conjunction with the accompanying drawings, which illustrate, by way of example, the principles of the invention.

DETAILED DESCRIPTION OF THE PREFERRED EMBODIMENT

Figure 1:
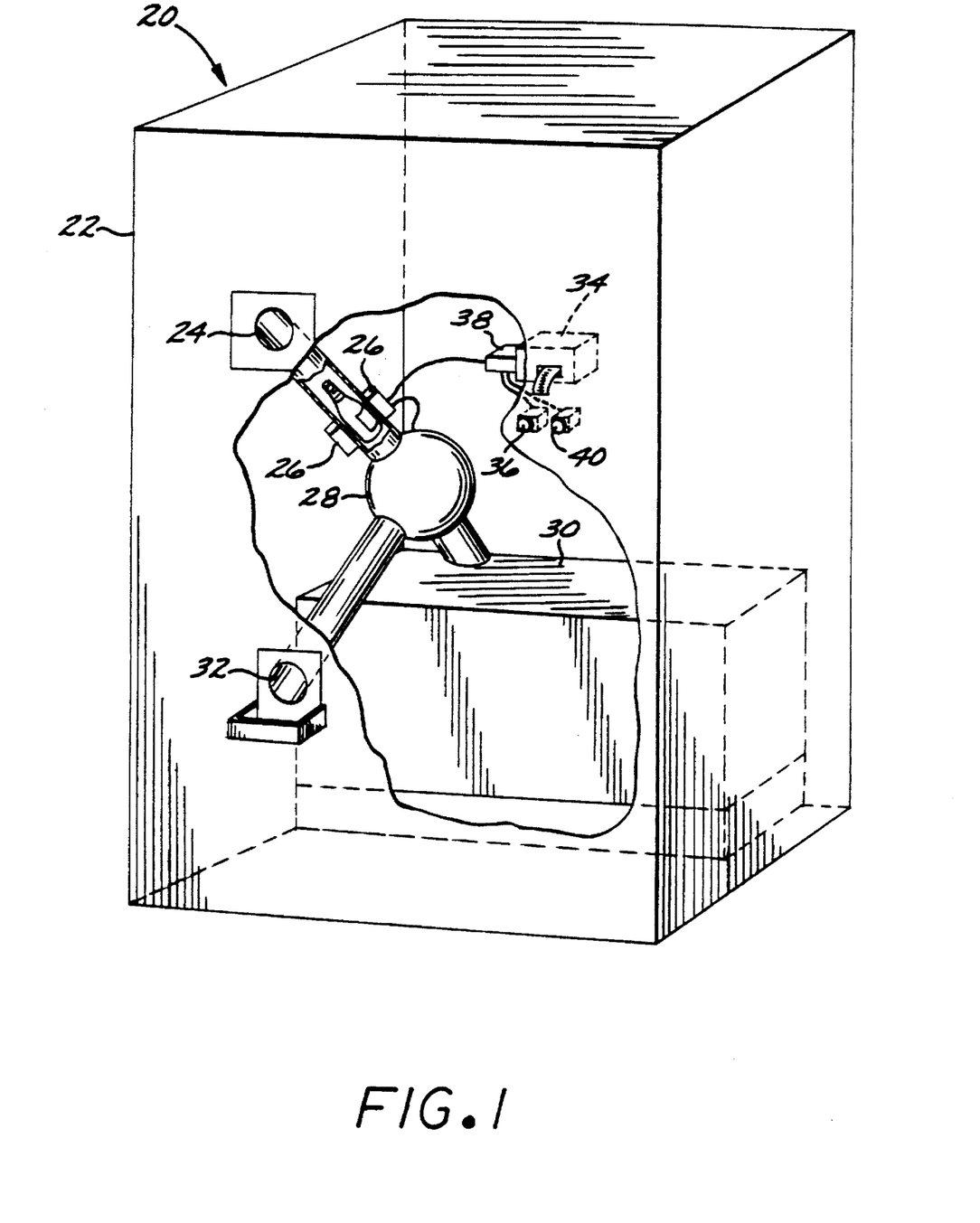
FIG. 1 is a perspective view of a recycling apparatus capable of employing the apparatus and process of the invention, with interior portions illustrated in cut-away view for clarity.

As illustrated in FIG. 1, the present invention includes a recycling apparatus 20 for receiving and sorting containers. The apparatus 20 includes a housing 22 having a receiving receptacle 24 therein, for receiving empty containers inserted therein by a customer. Containers received in the receptacle 24 pass through a sorting station 26, the operation of which is described in detail below. Sorted containers leave the sorting station 26 and travel through a sorting gate 28, and into one of a plurality of bins 30 for storage and/or crushing, or to a return chute 32 that returns unacceptable containers to the customer. The sorting gate 28 directs the container to a proper bin for storage or crushing, such as, for example, bin 30, or the return chute 32 under command of the sorting station 26.

A reward dispenser 34 delivers a reward to the customer for returning the containers, typically in the form of cash or coupons redeemable for goods, under control of a reward total accumulator 38. The reward dispenser typically permits the customer to choose whether the reward is to be in the form of cash or other type of available reward. On the face of the apparatus 20 is a start button 36 that signals the apparatus 20 that a particular customer is commencing the return of a series of one or more containers. Pressing the start button 36 causes the reward accumulator 38 to be set to zero. Each acceptable container sensed by the sorting apparatus 26 causes the reward accumulator 38 to be incremented by a proper amount, thereby keeping a running total of the reward due the customer. When the customer has deposited all the containers to be returned, an end button 40 is depressed to signal the reward accumulator 38 that the return process is completed. The reward accumulator 38 then provides an indication of the total reward to the customer. This indication may be purely visual, such as through an electronic display, or may be tangible, such as through a printed receipt. The structure of the recycling apparatus is known to those skilled in the art, except for the structure and operation of the sorting apparatus or station 26, and is described, for example, in U.S. Pat. Nos. 4,248,389, 4,248,334, and 4,919,534, the disclosures of which are incorporated herein by reference.

Figure 2:
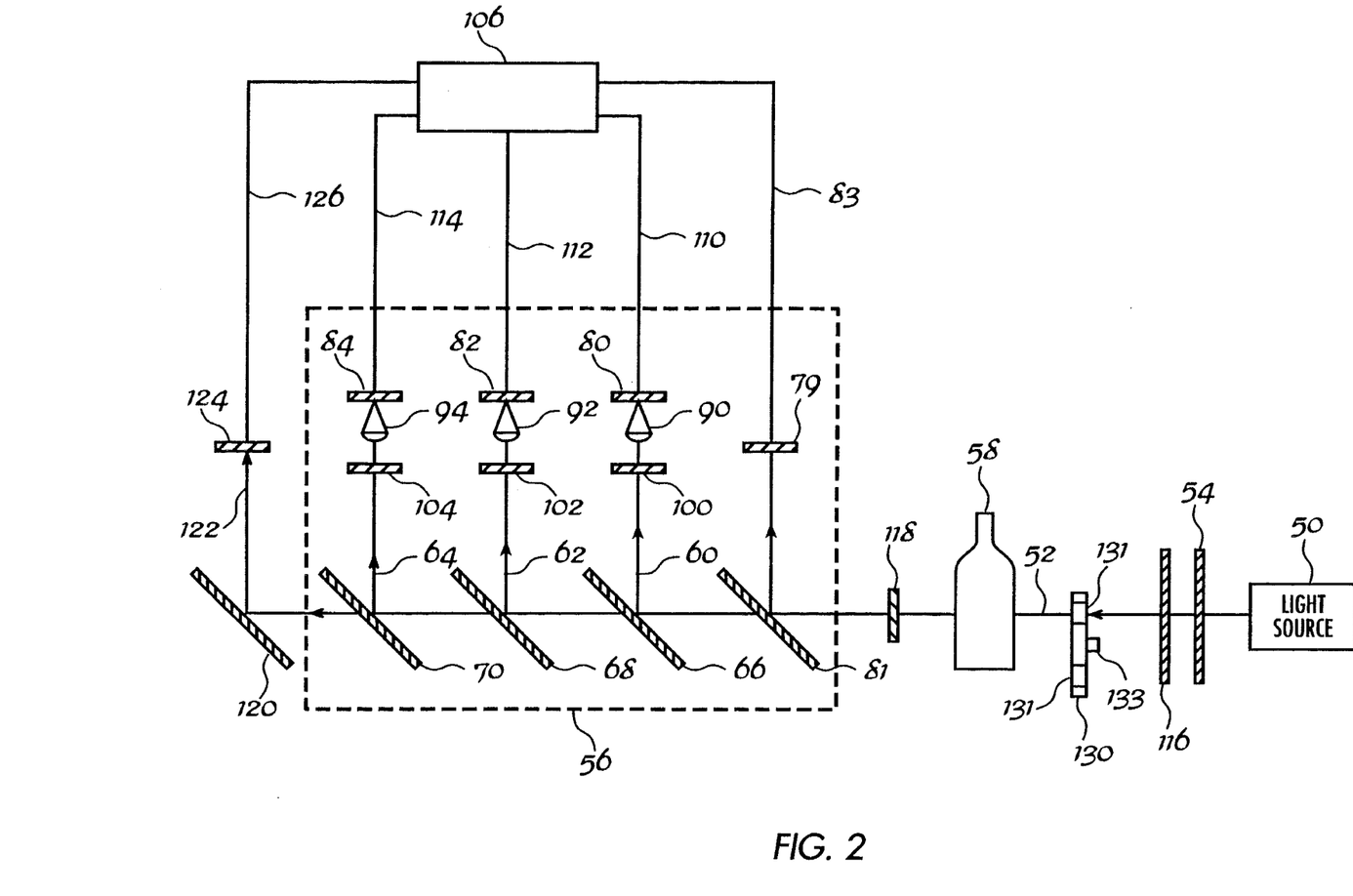
FIG. 2 is a schematic drawing of an apparatus in accordance with a first embodiment of the present invention for analyzing the character of a translucent container.

In accordance with the present invention, an apparatus for analyzing the character of a translucent container is provided and is shown schematically in FIG. 2. The apparatus includes a light source for directing a beam of light along an axis through a container. As embodied herein, a light source 50 is provided which directs a beam of light along an optical axis 52. Light source 50 may be, for example, a halogen lamp. If a halogen lamp is employed, an infrared filter 54 is disposed along the axis 52. Infrared filter 54 is required in such instances to prevent infrared light emanating from a light source such as a halogen lamp from falling incident on the detectors, described below, and rendering erroneous readings. Accordingly, infrared filter 54 is optional depending upon the type of light source used. Moreover, if a halogen lamp is used, it may be run at 80% power to increase life expectancy of the bulb.

Alternatively, light source 50 may be embodied as a fluorescent lamp operated at approximately 30 KHz. Emission of infrared radiation (IR) is substantially eliminated by embodying light source 50 as a fluorescent lamp. This eliminates the necessity for infrared filter 54. It is not intended to limit the present invention to use with any particular type of light source.

A first optical analyzer analyzes the color of the container. In one embodiment of the present invention, an embodiment of a first optical analyzer 56 is provided, shown in FIG. 2 enclosed within the box formed by dashed lines. First optical analyzer 56 may include means for directing portions of the beam of light that passed through the container along one or more sub-axis. As embodied herein and shown in FIG. 2, light that passes through container 58 propagates along optical axis 52 and is directed along one or more sub-axis, such as sub-axes 60, 62 and 64 by appropriate directing means which are described in detail below.

It is preferred, although not required, that light passing through container 58 pass through a single area in the container 58. That is, light of all wavelengths passes through the same area of container 58. In this manner, obstructions such as labels, inks, dyes, or the like are precluded from creating inaccuracies in the comparison of detected intensities of different wavelengths of light. The accuracy of such a comparison is assured by placing light source 50 on a common optical axis with the detectors (such as first, second and third detectors 80, 82, and 84, respectively, discussed below). Thus, signals from the detectors are taken at a rate fast enough, preferably simultaneously, that any movement of container 58 is insignificant, and measurements may be considered to have been taken through the same point on container 58. Container 58 may be moved through optical axis 52 as it traverses sorting station 26. In such cases, several sets of readings may be taken as container 58 passes through optical axis 52.

Moreover, an apparatus in accordance with the present invention may include an intensity detector to detect the intensity of light that has traversed container 58. As embodied herein and shown in FIG. 2, an intensity detector 79 is provided to which light is directed by a beam splitter 81. Intensity detector 79 is connected to microprocessor 106 through a connector 83. The signal from detector 79 is processed in a manner described below in reference to FIGS. 8 or 9 to determine if there is sufficient light to obtain an accurate reading from first, second, and third detectors 80, 82, and 84, respectively. If, for example, a label on container 58 is blocking the beam of light from light source 50, it may be necessary to reject container 58 to return chute 32 or signal the customer that container 58 must be repositioned for a proper reading.

Figure 4:
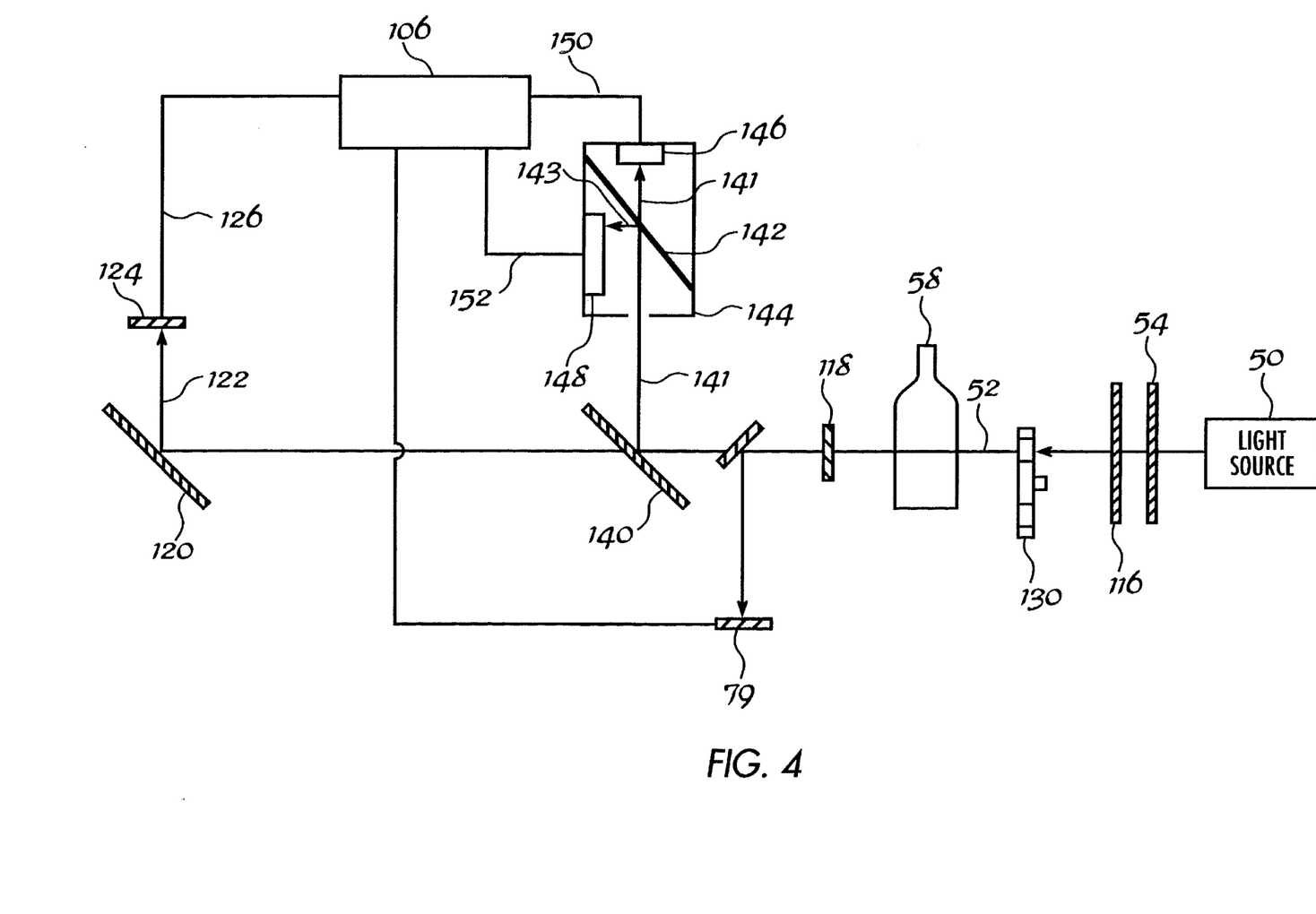
FIG. 4 is a schematic drawing of an apparatus in accordance with a second embodiment of the present invention for analyzing the character of a translucent container.

An apparatus in accordance with the present invention may include a light chopper. A light chopper is a device that allows light to pass along optical axis 52 on an intermittent basis. For example, as shown in FIGS. 2 and 4, a light chopper may be embodied as a wheel 130 having ports or passageways 131 at regular intervals near its perimeter. As wheel 130 is caused to rotate about its axis of rotation 133, light passes through passageways 131 along axis 52. When wheel 130 rotates to a point where there is no passageway 131 along axis 52, light emanating from light source 50 is blocked and will not pass along axis 52. In this way an intermittent beam of light passing along axis 52 is formed, the frequency of which is proportional to the speed of rotation of wheel 130 and the spacing of passageways 131 around the perimeter of wheel 130.

Wheel 130 may be embodied as any mechanical device that interrupts a light source at even intervals such as a fan or spinning wheel with slits in it. As an alternative to wheel 130, a light chopper may be embodied as a rotating mirror that bends light in and out of the optical path of the detectors.

Light emanating from light source 50 is chopped to create an AC type light signal of a known pulse width to filter out DC type light sources, such as daylight or incandescent light bulbs. This filtering out of DC type light sources is accomplished by synchronizing readings from the detectors to the chopper. In particular, this is accomplished by a band pass filter set to pass the desired frequency of signals from the detector and reject other frequencies. The means whereby the readings from the detectors are synchronized to the chopper are the same whether the chopper is embodied as a wheel, such as wheel 130, or any other structure, such as a rotating mirror.

Where light source 50 is embodied as a fluorescent lamp operated at approximately 30 KHz, the fluorescent lamp acts effectively as its own light chopper, thus eliminating the need for a light chopper.

In one embodiment of the present invention, the directing means includes a first, second and third wavelength-specific beam splitter. In this embodiment, light beams passing along the sub-axis contain light of wavelengths that differ from each other. As shown in FIG. 2, first, second and third wavelength-specific beam splitters, 66, 68, and 70, respectively, direct light propagating along optical axis 52 to first, second and third sub-axis 60, 62, and 64, respectively. As used herein, the term "wavelength-specific beam splitter" refers to any device which splits an incoming beam of light into two or more beams of light, each beam including light of a substantially different wavelength or range of wavelengths. A wavelength-specific beam splitter may be embodied, for example, as a dichroic mirror which reflects light of one wavelength, or of a desired range of wavelengths, and allows the remaining light in an incoming beam to pass through.

While dichroic filters provide a compact structure for splitting an incoming beam of light into two or more beams of light, the present invention is not limited to the use of dichroic filters. Indeed, directing means may be embodied by any device that separates light into wavelength specific beams. Suitable embodiments of the directing means may include, for example, reflectors, lenses, filters, diffusion gratings, prisms, or the like.

Where the directing means is embodied as a wavelength-specific beam splitter, it is preferred that the first wavelength-specific beam splitter direct substantially only blue light along a first sub-axis, the second wavelength-specific beam splitter direct substantially only green light along a second sub-axis, and the third wavelength-specific beam splitter direct substantially only red light along a third sub-axis. First, second and third wavelength-specific beam splitters, 66, 68, and 70, respectively, may be provided which direct substantially only blue, green and red light, respectively along first, second and third sub-axis 60, 62, and 64 respectively. Such an arrangement is preferred where detectors embodied as photodiodes are provided to detect light passing along sub-axis 60, 62, and 64. This is done because photodiodes are silicon devices. As a consequence they are less sensitive to blue than green light and less sensitive still to green than red light. Thus, the order described above is preferred since the light reaching a photodiode detecting blue light will have gone through fewer filtering steps than light reaching a photodiode detecting green or red light. Similarly, light reaching a photodiode detecting green light will have gone through fewer filtering steps than light reaching a photodiode detecting red light.

One or more detectors corresponding to the one or more sub-axes are provided to generate signals in response to light incident thereon. As embodied herein and shown in FIG. 2, first second, and third detectors 80, 82, and 84, respectively, are provided along first, second, and third sub-axis 60, 62, and 64, respectively. Preferably, the apparatus includes a first, second and third focussing lens 90, 92, and 94, respectively disposed along first, second, and third sub-axis 60, 62, and 64, respectively, for focussing light on first, second, and third detectors 80, 82, and 84, respectively. The first, second and third focussing lenses 90, 92, and 94, respectively, may be embodied as cabishon lenses. A cabishon or half-sphere lens has a short focal length. This allows for a more compact design and fabrication of the apparatus in accordance with the present invention.

In one embodiment of the present invention, the apparatus includes first, second and third color correcting filters 100, 102, and 104, respectively, disposed along said first, second, and third sub-axis 60, 62, and 64, respectively. The correcting filters 100, 102, and 104 are filters having a sharper transmission curve than the reflective curves of the corresponding wavelength-specific beam splitters 66, 68, and 70. The color correcting filters effectively eliminate unwanted wavelengths that are reflected from the beam splitter. Each of the first, second and third color correcting filters 100, 102 and 104 work in pairs with the corresponding wavelength-specific beam splitters 66, 68, and 70, respectively. This provides a clean three color separation of the light transmitted through a container.

The color correcting filters 100, 102, and 104, as well as the wavelength specific beam splitters 66, 68, and 70 may be made using a substrate of any suitable material, such as glass, pyrex, or borosilicate.

The determining means detects the color of the container depending upon the relative magnitudes of the signals from the one or more detectors. Determining means in accordance with the present invention may be embodied, for example, as a microprocessor 106. Further details of the determining means are described below in reference to FIGS. 3 and 7.

First, second and third detectors 80, 82, and 84, respectively, are connected to microprocessor 106 through first, second and third connectors 110, 112, and 114, respectively.

Figure 3:
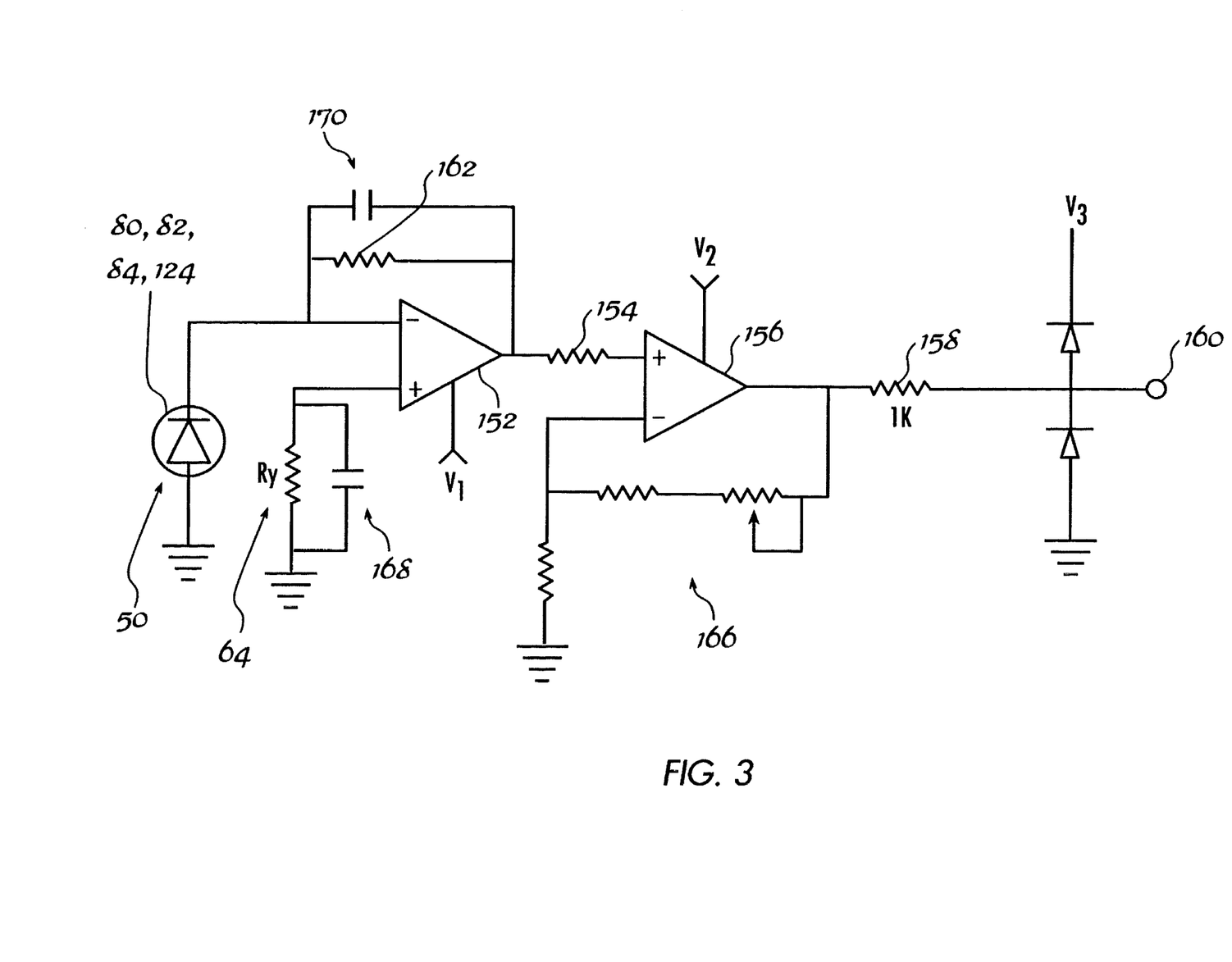
FIG. 3 is an embodiment of an electronic circuit useful in the first embodiment of the present invention shown in FIG. 2.

By way of example and not limitation, one possible set of electronics for the embodiment of FIG. 2 are shown in FIG. 3. The optical detector, such as one of the detectors 80, 82, or 84 which is preferably a photodiode, is connected across the inputs of a first operational amplifier 152. The output is coupled through a resistor 154 to the input of a second operational amplifier 156. The output of second operational amplifier 156 is coupled through a resistor 158 to an output port 160. It is preferred that first operational amplifier 152 have a feedback resistor 162 having a resistance Rx. The value, Rx, of feedback resistor 162 depends upon whether detector 80, 82, or 84 is detecting red, green or blue light. Similarly, first operational amplifier 152 has an input resistor 164 having a resistance Ry. The value, Ry, of input resistor 164 depends upon whether detector 80, 82, or 84 is detecting red, green or blue light.

In one embodiment, the circuit shown in FIG. 3 operates in the following manner. The signals from detectors 80, 82, and 84, are first amplified and converted to a scaled voltage to provide a zero to 4.5 volt signal—zero volts corresponding to a situation where no light is incident on a detector and 4.5 volts (the full-scale value) corresponding to a situation where the beam emanating from light source 50 is uninterrupted. The latter situation exists, for example, where there is no container 58 interrupting the beam emanating from light source 50. The introduction of a container will cause the values to drop to a level representing the transmissive value for each of the color bands.

The following table provides an example of an embodiment of the value of Rx, Ry and Vout, where Vout is the voltage at output port 160 where no container is present:

|  | Rx | Ry | Vout (No Container) |
| --- | --- | --- | --- |
| Red | 100K | 100K | 4.5 VDC |
| Green | 510K | 510K | 4.5 VDC |
| Blue | 180K | 180K | 4.5 VDC |

Second operational amplifier 156 includes an adjustable feedback resistance circuit 166. Thus, by setting $V_1$, $V_2$, and $V_3$ to −12 VDC, +12 VDC and 5 VDC, respectively the full-scale output at output port 160 for red, green, blue light can be set at 4.5, 4.5, and 4.5 VDC, respectively, when no container is present. In such an embodiment first and second capacitors, 168 and 170, respectively, are selected to have a capacitance of 0.01 mf and 1.5 mf, respectively.

In the preferred embodiment, these scaled voltage values are passed to an analog to digital converter that is under the control of microprocessor 106. The analog data may be interpreted to identify the color of container 58 in the following manner. The analog to digital converter converts the scaled voltages to a digital value. The digital values are stored by microprocessor 106 as sets in a R.A.M. included in microprocessor 106. Microprocessor 106 calculates ratios of red to green, and green to blue, and blue to red based upon the stored digital values. A comparison of the calculated ratios to standard ratio values provides the determination of the container's color. The comparison is done in microprocessor 106.

Standard ratio values are values that were derived empirically by the sampling of beverage containers of each color from a wide range of manufacturer's products. The data obtained from this sampling was then calculated to derive standard ratio values for a given color. As an example, clear glass would lower the light intensity of all three color values but have little effect on the ratio of one color to another. Green containers reduce the blue and red values as a ratio to green. Amber reduces the green and blue to red ratio.

Preferably, the apparatus includes a second analyzer for determining if the container includes an optically active material. An optically active material is one that rotates the direction of polarization of light passing through it. For example, it is known that PET rotates light about 35° to 40° whereas vinyl is not optically active and does not, therefore, rotate light that passes through it. With reference to FIG. 2, the second analyzer includes a polarizer disposed between the light source and the container for polarizing light emanating from the light source in a first polarizing direction. As embodied herein, a first polarizer 116 is provided along optical axis 52 to intercept light emanating from light source 50. A cross polarizer is disposed along the axis to intercept light that passes through the container. As embodied herein, a cross polarizer 118 is provided to intercept light passing along optical axis 52 that passes through container 58. Cross polarizer 118 has a second polarizing direction cross to said first polarizing direction. Polarizing material useful for first polarizer 116 and cross polarizer 118 in accordance with the present invention is available from the Polaroid Corporation.

By passing polarized light through a PET container a rotation of the light may be observed. If the polarized light used for this purpose is polarized at 45 degrees to the long axis of the container, a cross polarizer 118 at 90 degrees to first polarizer 116 is placed opposite container 58. Consequently, when no container is present there will be no light transmitted from the source through cross polarizer 118.

Conversely, if a container 58 made of PET is introduced between the two polarizers, light passing through the container 58 will be rotated in such a way as to allow it to pass through cross polarizer 118 and be detected at fourth (PET) detector 124.

Directing means are provided to direct at least a portion of the beam of light along a fourth sub-axis 122. As shown in FIG. 2, directing means 120 are provided which direct at least a portion of the beam of light passing along optical axis 52 along a fourth sub-axis 122. Preferably, directing means 120 is a mirror disposed along axis 52 and at an angle to axis 52.

A polarization (PET) detector 124 is disposed along fourth sub-axis to intercept light and detect the intensity of the beam of light passing along the fourth sub-axis. Polarization (PET) detector 124 generates a polarization signal in proportion to the intensity of light incident thereon and sends the signal along a line 126 to microprocessor 106. Microprocessor 106 determines whether the container includes an optically active material depending upon the magnitude of the polarization signal. Determining means may include an electronic circuit such as that shown in FIG. 3 to make such a determination. The electronic circuit of FIG. 3 in this application would be as described above, with the exception that Rx and Ry=1 meg ohms and $V_o$=1.2 VDC. $V_o$ is digitized to produce a 0 to 255 count value. The analog signal is passed to an analog to digital converter that is under control of microprocessor 106. The analog data that may be interpreted into identification of containers made of PET material. The value with no container may be set at 126 counts out of a possible 255. The count rises above 200 for acceptable materials and generally goes below 100 for non-active materials. While cross polarizer 118 is shown in FIG. 2 as being disposed adjacent container 58, it should be understood that cross polarizer 118 may be located at any point along axis 52 between container 58 and polarization (PET) detector 124.

Methods and apparatuses currently exist for determining the color and composition of a material by reading a barcode. A "barcode" is a specific arrangement of bars or elements that contains information such as an identification of the product to which it is affixed, as well as the color and/or material of which the container is made. Thus, by reading the barcode the material and color of the container can be determined. If the barcode or label containing a barcode are deliberately or inadvertently placed on the wrong container, an erroneous determination of that container's color and/or composition may result. Accordingly, the present method and apparatus provides a way to verify that the information included in the barcode is accurate. This is particularly useful where, in addition to sorting containers by color and composition, it is desirable to keep a record of the manufacturer and/or distributor of the containers. It should be understood, however, that the present invention is useful in a system where the barcode is not read at all.

Another embodiment of the present invention is shown in FIG. 4. The description of the elements of the embodiment of the present invention shown in FIG. 4 is the same as for corresponding elements of the embodiment shown in FIG. 2 which bear the same reference numerals.

In the embodiment of the invention as shown in FIG. 4, a first optical analyzer for analyzing the color of light passing through a container is provided which includes a first directing means for directing portions of said beam of light passing through said container along one or more sub-axes. As described above in reference to FIG. 2, a beam of light emanates from light source 50 and propagates along axis 52, passing through container 58.

Light propagating along axis 52 encounters directing means. As shown in the embodiment of the present invention of FIG. 4, the directing means includes half-mirrors 140 and wavelength-specific beam splitter 142. Half-mirror 140 reflects a desired portion of the light propagating along axis 52 and allows substantially all of the remainder to pass through. The portion of the light reflected by half-mirror 140 propagates along a sub-axis 141. Wavelength-specific beam splitter 142 is disposed along sub-axis 141 and reflects a first portion of the light propagating along sub-axis 141 and allows substantially all of the remainder, a second portion, to pass through. The first portion, light reflected by wavelength-specific beam splitter 142, propagates along a sub-axis 143. The range of wavelengths of light contained in the first and second portions may be chosen, for example, to calculate the wavelength of light passing through container 58 in the manner described below in reference to FIG. 7.

As shown in FIG. 4, one or more detectors corresponding to said one or more sub-axes are provided. In particular, a detector 146 is provided along sub-axis 141 and a detector 148 is provided along sub-axis 143. Each of the detectors 146 and 148 generate signals in response to light incident thereon.

Figure 5:
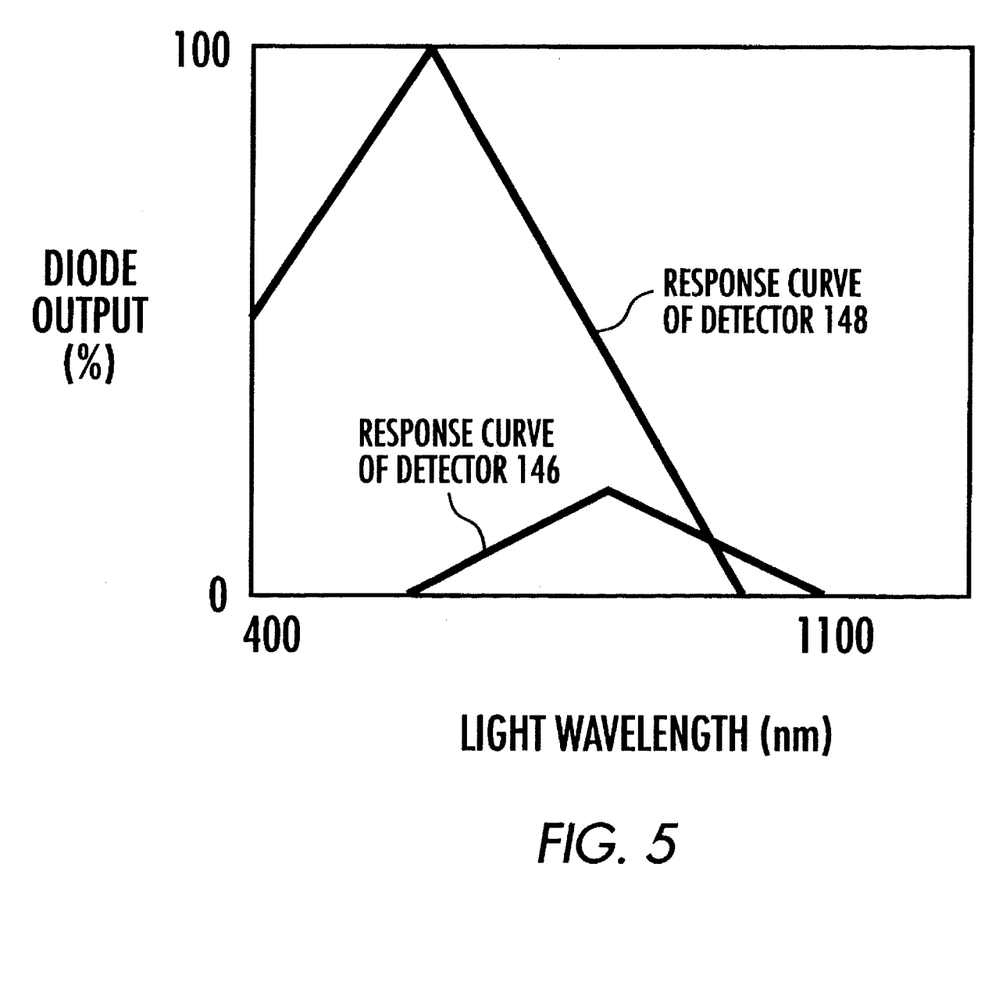
FIG. 5 is a graph of output from light detectors as a function of the wavelength of light useful in the second and third embodiments of the present invention shown in FIGS. 4 and 6, respectively.

Means are provided for determining the color of a container depending upon the relative magnitudes of the signals from the one or more detectors. In the embodiment of the present invention shown in FIG. 4, two photo diodes having different response curves are used. As an example, response curves of two photodiodes useful in an apparatus and method of the present invention are shown in FIG. 5. The output of the photodiodes 146 and 148 are fed into microprocessor 106 along lines 150 and 152. The color of container 58 is then determined in a manner described below in reference to FIG. 7.

Figure 6:
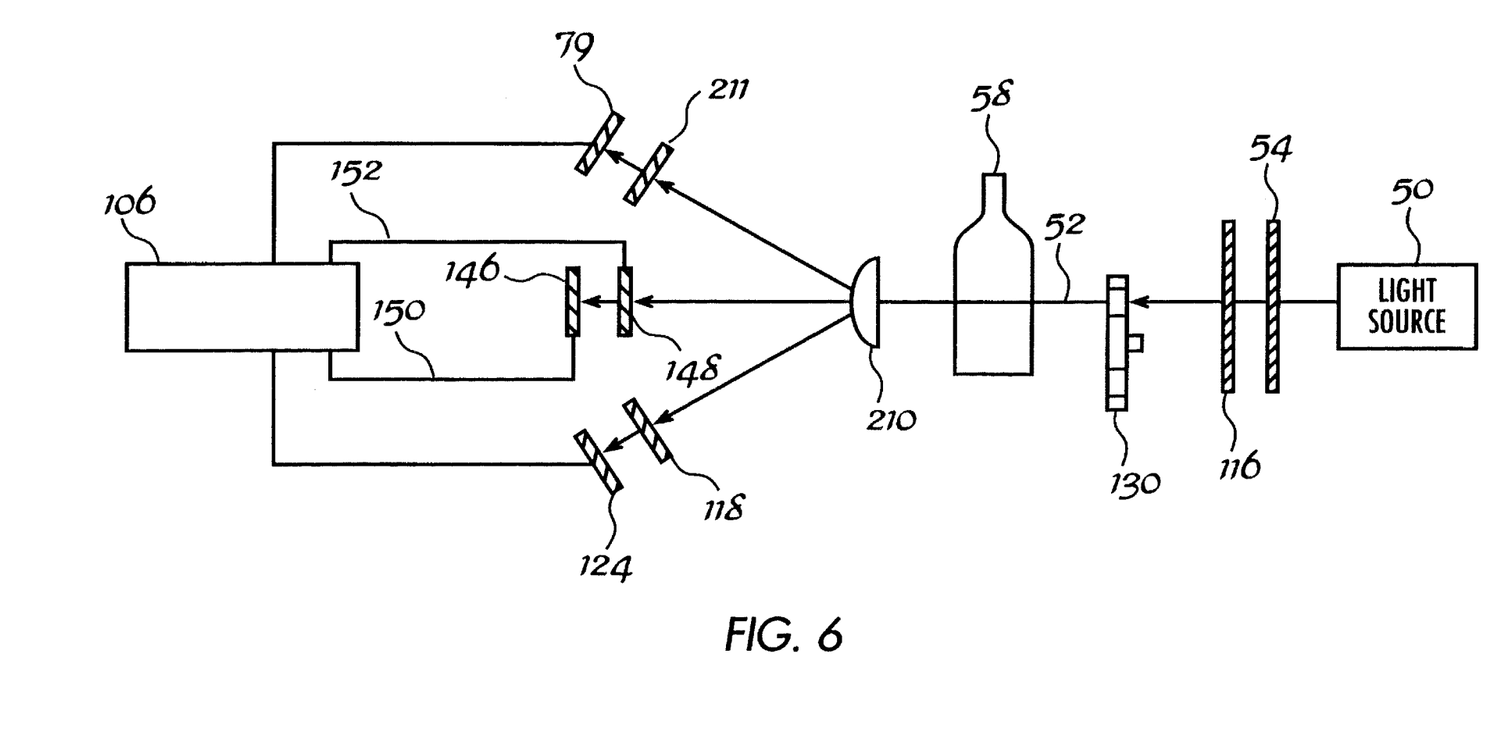
FIG. 6 is a schematic drawing of an apparatus in accordance with a third embodiment of the present invention for analyzing the character of a translucent container.

A third embodiment of the present invention is as shown in FIG. 6. The description of the elements of the embodiment of the present invention shown in FIG. 6 is the same as for corresponding elements of the embodiment shown in FIGS. 2 and 4 which bear the same reference numerals.

In the embodiment of the invention as shown in FIG. 6, a first optical analyzer for analyzing the color of light passing through a container is provided which includes a first directing means for directing portions of said beam of light passing through said container along one or more sub-axis. As described above in reference to FIG. 2 and 4, a beam of light emanates from light source 50 and propagates along axis 52, passing through container 58. Light propagating along axis 52 encounters directing means. In accordance with the present invention, the directing means may be embodied as a defocussing device 210. Defocussing device 210 may be embodied, for example, as a lens, but may also be embodied as a diffraction grating, a holographic optical element or the like. The purpose of defocussing device 210 is to spread the beam of light propagating along axis 52 to an extent at least sufficient to illuminate detectors 124, 146, 148 and 79.

As shown in FIG. 6, one or more detectors are provided. As in the embodiment shown in FIG. 4, each of detectors 146 and 148 generate signals in response to light incident thereon. Unlike the embodiment in FIG. 4, detector 148 is disposed to intercept light passing through defocussing device 210 while detector 146 is disposed behind detector 148 so as to intercept light emanating from detector 148. In such an embodiment the two detectors 146 and 148 are vertically incorporated into one chip with the first (detector 148) acting as an optical filter with respect to the second (detector 146). For example, light of a short wavelength is absorbed by detector 148 while light of a long wavelength will penetrate deeper to detector 148. Thus, the first detector 148 is more responsive to short wavelengths of light while second detector 146 is more responsive to longer wavelengths of light. Detectors 146 and 148 may be embodied as, for example, a model PD150 color sensor available from Sharp Corporation.

In the embodiment of the present invention shown in FIG. 6, cross polarizer 118 is placed directly in front of polarization (PET) detector 124. Indeed, while cross polarizer 118 in the embodiment of FIG. 2 is shown intercepting all light passing through container 58, it may be disposed directly in front of polarization (PET) detector 124 as well.

There may be instances in which the distribution of light from defocussing device 210 on intensity detector 79, color detectors 146 and 148 and polarization (PET) detector 124 may be uneven. This may be caused, for example, by imperfections in container 58 and/or container 58 acting as a lens. Moreover, there may be containers that cause a circular polarization of light, rather than a shift in the plane polarization, as in the case of PET containers, or no polarization shift at all, as in the case of glass. Such an uneven distribution of light or circular polarization may be detected in the following manner.

A polarizing filter 211 may be placed in front of intensity detector 79. Polarizing filter 211 is preferably a plane polarizing filter and oriented parallel to the direction of polarization of light passing through filter 116. Placing polarizing filter 211 in front of intensity detector 79 causes a relative shift in the signals from intensity detector 79 and polarization (PET) detector 124. In particular, when a glass container, or no container at all, is placed in the position of container 58, the intensity of light incident on intensity detector 79 will be high relative to the intensity of light incident on polarization (PET) detector 124. Conversely, when a PET container is placed in the position of container 58, the intensity of light incident on intensity detector 79 will be low relative to the intensity of light incident on polarization (PET) detector 124.

In either case, there should be a substantially equal and opposite shift of the level of signals from intensity detector 79 and polarization (PET) detector 124. The introduction of a container 58 that causes an unsymmetrical or unequal shift indicates that the distribution of light between intensity detector 79 and PET detector is uneven. This uneven distribution may be caused by, as indicated above, an imperfection in container 58 or a container 58 that is configured and oriented so as to act as a lens. Moreover, an unsymmetrical or uneven signal level from intensity detector 79 and polarization (PET) detector 124 may indicate the presence of a container 58 made of a material that causes circular polarization of light. Such materials are contaminants to the PET material, including impact polystyrene or stretched polyethylenes.

Microprocessor 106 includes means for determining when the shift of signal levels from intensity detector 79 and polarization (PET) detector 124 is not equal and opposite. These means may be embodied, for example, as comparators which compare the digitized values from the PET and intensity detectors. In such instances, container 58 may be rejected at sorting gate 28 and returned, via return chute 32, to the customer.

Means are provided for determining the color of a container depending upon the relative magnitudes of the signals from the one or more detectors. In the embodiment of the present invention shown in FIG. 6, as in the case of the embodiment of FIG. 4, two photo diodes having different response curves are used. As an example, response curves of two photodiodes useful in an apparatus and method of the present invention are shown in FIG. 5. The output of the photodiodes 146 and 148 are fed into microprocessor 106 along lines 150 and 152, respectively. The color of container 58 is determined in a manner described below in reference to FIG. 7.

Figure 7:
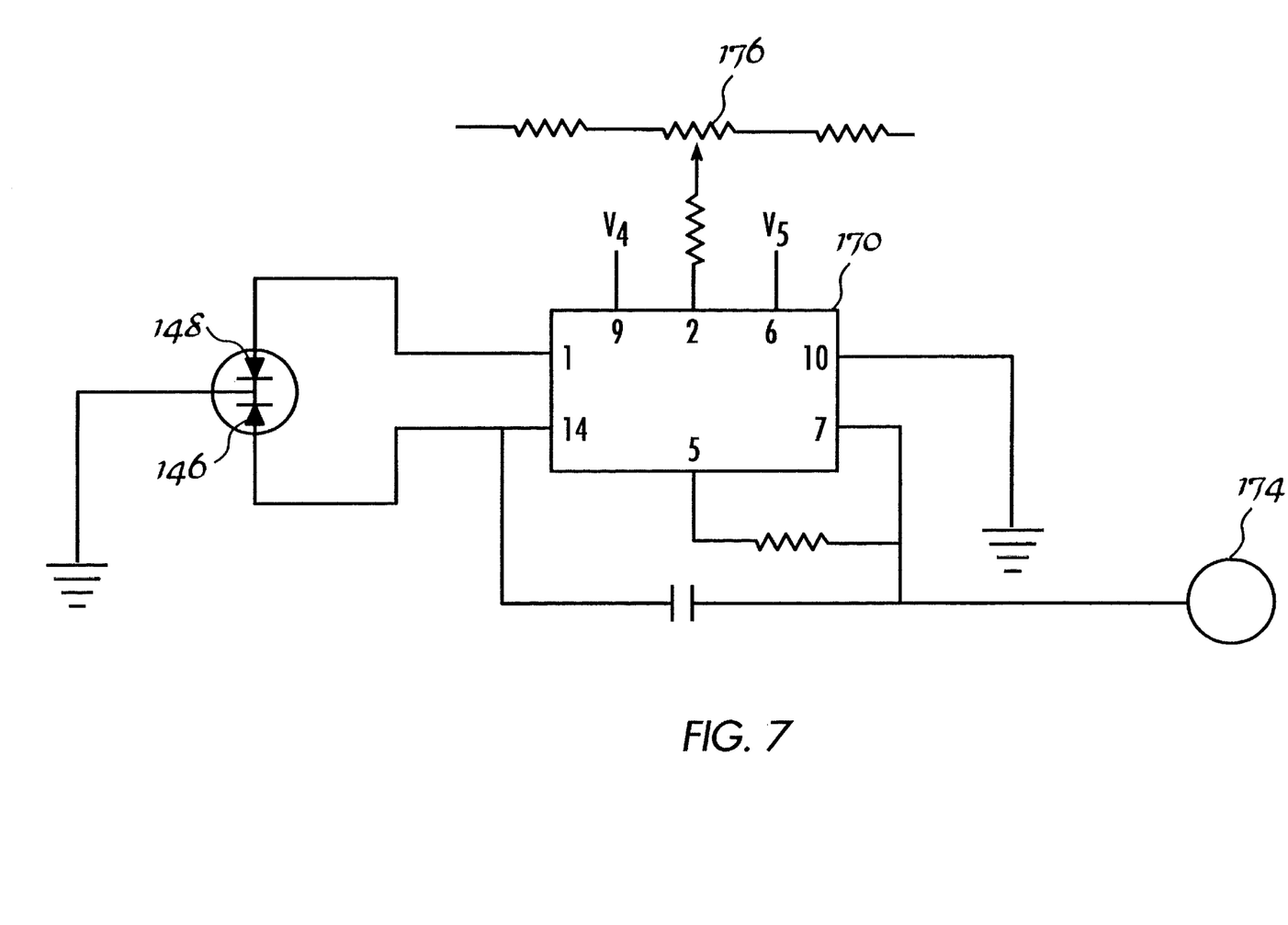
FIG. 7 is an embodiment of an electronic circuit useful in the second embodiment of the present invention shown in FIG. 4 for determining the color of light passing through a container.

Referring to FIGS. 4 or 6 and 7, detectors 146 and 148, which are preferably photodiodes, are connected to an integrated circuit 170 contained in microprocessor 106. Integrated circuit 170 is preferably a model LOG 100 JP log amp manufactured by Burr Brown. Detectors 146 and 148 are chosen such that each is responsive to a different range of wavelengths of light. For example, as shown in FIG. 5, photodiode 148 is more responsive at shorter wavelengths as compared to photodiode 146. In this way a relationship between the ratio of short circuit currents from photodiodes 146 and 148 and the wavelength of incident light ($\lambda$) can be obtained.

Each of the short circuit currents $I_{sc1}$ and $I_{sc2}$ obtained from photodiodes 146 and 148, respectively, is logarithmically compressed and goes through a subtraction circuit in integrated circuit 170 to produce a reduced output voltage. The reduced output voltage from integrated circuit 170 is adjustable for wavelengths in the range 400 to 700 nm through adjustable resistor 176 to provide, preferably, an output voltage of −12 to +12 VDC over a wavelength range of 400 to 700 nm. Integrated circuit 170 is supplied with a voltage through a voltage source to provide a voltage at $V_4$ preferably −12 VDC and a voltage at $V_5$ of preferably +12 VDC. Thus, the electronic circuit of FIG. 7 solves for $V_o$ as follows:

$$V_o = \log I_{sc1} - \log I_{sc2} = \log (I_{sc1}/I_{sc2});$$

where $I_{sc1}$=the short circuit current of the first detector; and $I_{sc2}$=the short circuit current of the second detector.

The voltages at output port 174 are preferably clipped to 0 to 5 VDC. The voltage at output port 174 when no container is present is adjusted to 2.50 VDC.

Figure 8:
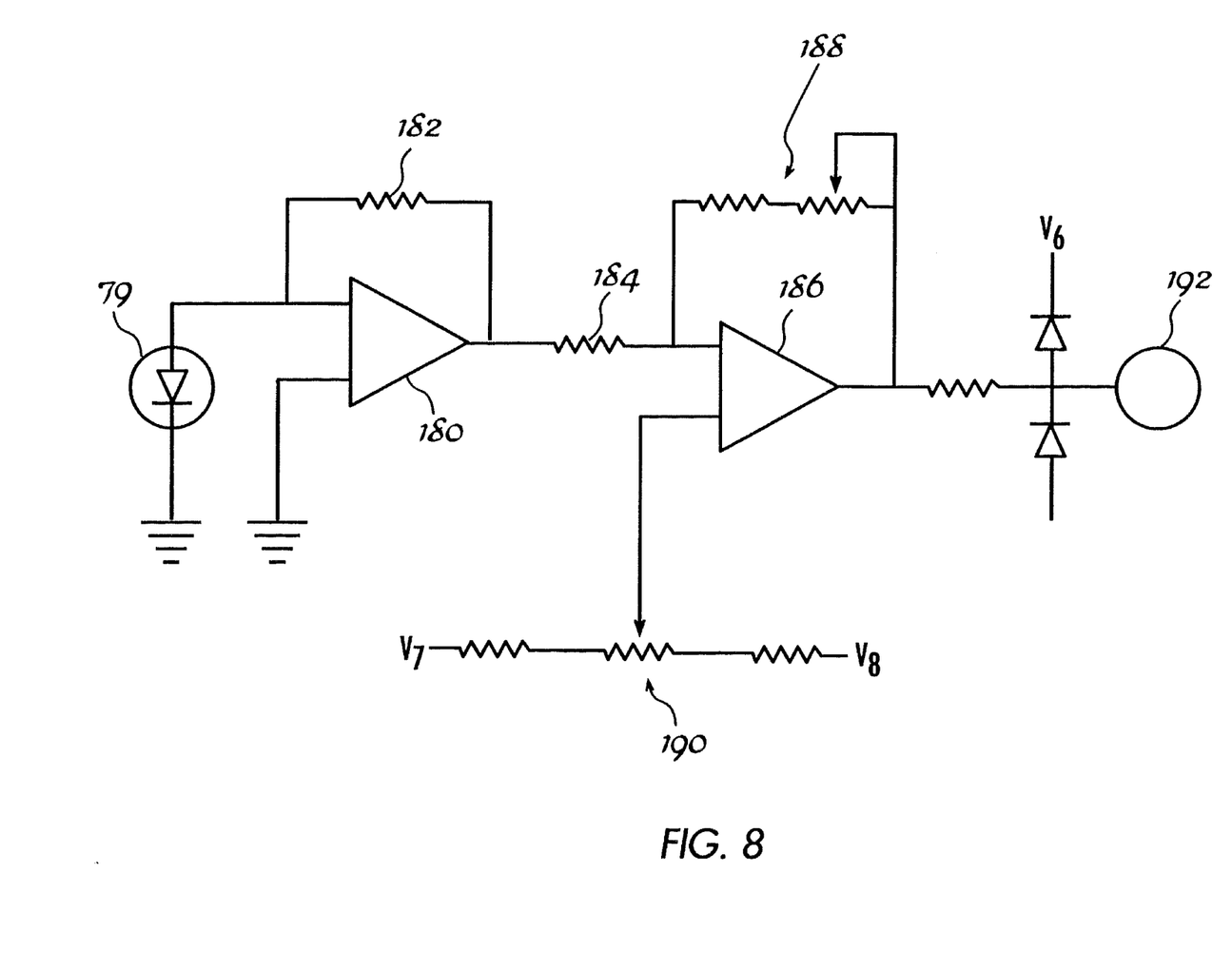
FIG. 8 is an first embodiment of an electronic circuit useful for determining the intensity of light passing through a container.

The intensity of light that propagates through container 58 is measured through electronic circuitry embodied, for example, as shown in FIG. 8. Light is incident on a detector 79, preferably a photodiode, and is connected across the inputs of an operational amplifier 180. In a preferred form, operational amplifier 180 has a 120 k-ohm feedback resistor 182. The output of operational amplifier 180 is coupled through a resistor 184 to the input of another operational amplifier 186. The value of feedback resistor 190 is adjustable to provide an output voltage at output port 192 of 0 to 5 VDC given an output from photodiode 79 of 0.0 to 4,000 nA and an output from operational amplifier 180 from 0.0 to 0.9 VDC.

Figure 9:
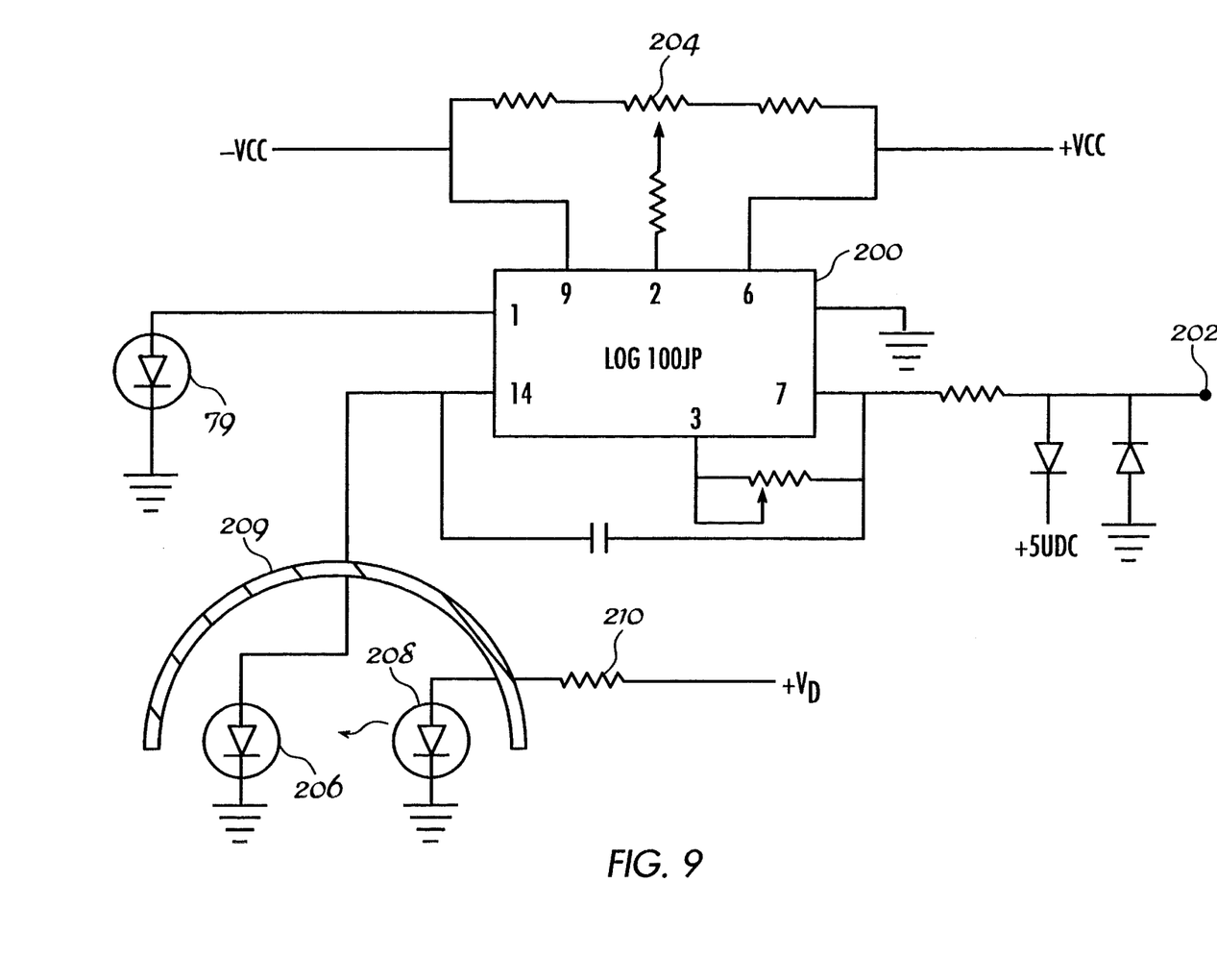
FIG. 9 is a second embodiment of an electronic circuit useful for determining the intensity of light passing through a container.

An alternative embodiment of the electronics for processing the signal from intensity detector 79 is shown in FIG. 9. Intensity detector 79, preferably a photodiode, is connected to an integrated circuit 200 which is contained in microprocessor 106. Integrated circuit 200 is preferably a model LOG 100 JP log amp manufactured by Burr Brown. The current from detector 79 is logarithmically compressed and goes through a subtraction circuit in integrated circuit 200 to produce a reduced output voltage at output port 202. The output voltage is adjustable through adjustable resistor 204 to provide, preferably, an output voltage of 0 to 5 UDC. Integrated circuit 200 is supplied with a voltage through a voltage source to provide a voltage at −VCC of, preferably, −12 VDC and at +VCC of preferably, +12 UDC. The voltages at output port 202 are preferably clipped to 0 to 5 UDC. Detector 79 is preferably embodied as a BPW 34 photodetector available from Siemens Corp.

The reference current (IREF) at pin 14 of integrated circuit 200 is preferably in the range of 18 to 30 nanoamps and, most preferably 22 nanoamps. A stable current source at that level is difficult to obtain. Accordingly, a preferred source is the combination of photodetector 206 and LED 208 shown in FIG. 4. LED 208 is connected through resistor 210 to a voltage source, $V_D$. Voltage source $V_D$ is preferably +5 UDC and resistor 210 has, preferably, a resistance of 12K ohm. The light from LED 208 falls incident on photodetector 206 whereupon photodetector 206 produces current in the desired range. Photodetector 206 may be embodied as a BPW 34 photodetector from Siemens Corp. Preferably, photodetector 206 and LED 208 are shielded by a light shield 209 to prevent stray ambient light from impinging on photodetector 206 which would cause an erroneously high output therefrom.

A preferred embodiment of an electronic circuit for determining the presence of PET in a device in accordance with the second and third embodiments of the present invention shown in FIGS. 4 and 6, respectively, may be the same as described above in reference to FIG. 3.

Alternatively, an electronic circuit for determining the presence of PET in a device in accordance with the second embodiment may be the same as shown in FIG. 8 with the exception that variable resistors 188 and 190 are adjusted to provide a voltage at the output port of 0 to 5 VDC with an output from photo diode of 0 to 2,100 nA and operational amplifier 180 of 0.0 to 0.9 VDC.

The system described hereinabove has been constructed and used to correctly measure the color index of containers and to distinguish between PET and non-PET containers. It provides a clear signal to sort containers on these bases. Thus, the present approach provides an apparatus and process for distinguishing and sorting transparent and partially transparent containers by material of construction and color, without the need for human intervention. Although particular embodiments of the invention have been described in detail for purposes of illustration, various modifications may be made without departing from the spirit and scope of the invention. For example, log amps may also be used for the intensity and PET measurements. This provides an extended sensitivity range through data compression. Accordingly, the invention is not to be limited except as by the appended claims.

What is claimed is:

1. An apparatus for analyzing a character of a translucent container, comprising:

a light source having multiple wavelengths emitted simultaneously for directing a beam of light along a single optical axis through the container, said multiple wavelengths contained in said beam of light being simultaneously directed along said optical axis through the container;

a first optical analyzer for analyzing a color of light passing through the container, including
one or more detectors for generating signals in response to light incident thereon;
first directing means for directing one or more portions of said beam of light passing through the container toward said one or more detectors; and
means for determining a color of the container depending upon relative magnitudes of said signal from said one or more detectors.

2. An apparatus as claimed in claim 1, further comprising a second analyzer for determining if the container includes an optically active material, including:

a polarizer disposed between said light source and the container for polarizing light emanating from said light source in a first polarizing direction;

a cross polarizer disposed along said optical axis to intercept light passing though the container having a second polarizing direction cross to said first polarizing direction;

a polarization detector for detecting light passing through said cross polarizer and generating a polarization signal in proportion thereto; and means for determining whether the container includes an optically active material depending upon a magnitude of said polarization signal.

3. An apparatus as claimed in claim 2, wherein said means for determining whether the container includes an optically active material includes an amplifier for amplifying said polarization signal and a comparator for comparing the amplified signal to a reference value and generating a signal indicative of optically active material in the container when said amplified polarization signal meets or exceeds said reference value.

4. An apparatus as claimed in claim 2 further including second directing means for directing at least a portion of said beam of light toward said polarization detector.

5. An apparatus as claimed in claim 4, wherein said second directing means comprises a mirror disposed along and oblique to said axis.

6. An apparatus as claimed in claim 2, wherein said light source is a fluorescent light operated at approximately 30 KHz.

7. An apparatus as claimed in claim 1, further comprising an intensity detector for detecting an intensity of light passing through the container.

8. An apparatus as claimed in claim 1, further including a light chopper to chop the light emanating from the light source at predetermined intervals.

9. An apparatus as claimed in claim 1, wherein said first directing means includes a lens.

10. An apparatus as claimed in claim 1, wherein said light source is a halogen light.

11. An apparatus as claimed in claim 1, further including a container support for supporting said container when light from said light source is directed therethrough.

12. An apparatus as claimed in claim 1, wherein said one or more detectors includes a color-specific detector corresponding to each of the wavelengths of light to be detected.

13. An apparatus for analyzing a character of a translucent container, comprising:

a light source having multiple wavelengths emitted simultaneously for directing a beam of light along a single optical axis through the container, said multiple wavelengths contained in said beam of light being simultaneously directed along said optical axis through the container;

a first optical analyzer for analyzing a color of the light passing through the container, including
one or more detectors for generating signals in response to light incident thereon;
first, second and third wavelength-specific beam splitters for directing one or more portions of said beam of light passing through the container along first, second and third sub-axes, respectively toward said one or more detectors; and
means for determining a color of the container depending upon relative magnitude of said signals from said one or more detectors.

14. An apparatus as claimed in claim 13, wherein said first wavelength-specific beam splitter directs substantially only blue light along said first sub-axis, said second wavelength-specific beam splitter directs substantially only green light along said second sub-axis and said third wavelength-specific beam splitter directs substantially only red light along said third sub-axis.

15. An apparatus as claimed in claim 13, including a first, second and third focussing lens disposed along said first, second, and third sub-axis respectively, for focussing light on first, second and third detectors, respectively.

16. An apparatus as claimed in claim 15, further including an infrared filter along the optical axis in a path of light emanating from said light source.

17. An apparatus as claimed in claim 13, wherein said first, second and third focussing lenses comprise cabishon lenses.

18. An apparatus as claimed in claim 13, including first, second, and third color correcting filters disposed along said first, second and third sub-axes, respectively.

19. An apparatus for analyzing a character of a translucent container, comprising:

a light source having multiple wavelengths for directing a beam of light along a single optical axis through the container, said multiple wavelengths contained in said beam of light being simultaneously directed along said optical axis through the container;

a first optical analyzer for analyzing a color of the light passing through the container, including
a first detector and a second detector for generating signals in response to light incident thereon, each of which is responsive to a different range of wavelengths of light;
first directing means for directing one or more portions of said beam of light passing through the container toward said one or more detectors; and
means for determining a color of the container depending upon relative magnitudes of said signals a logarithmic subtraction circuit that solves for $V_o$, a from said one or more detectors, said determining means including a logarithmic subtraction circuit that solves for $V_o$, a voltage output of said determining means proportional to the wavelength of light passing through the container, where $$V_o = \log I_{sc1} - \log I_{sc2} = \log (I_{sc1}/I_{sc2});$$

$I_{sc1}$=a short circuit current of said first detector; and
$I_{sc2}$=a short circuit current of said second detector.

20. An apparatus as claimed in claim 19, wherein said first and second detectors are on a common optical axis such that light traverses said first detector to said second detector.

21. An apparatus as claimed in claim 19, wherein said first portion directing means includes a beam splitter to direct a first portion and a second portion of the beam of light passing through the container to said first and second detectors, respectively.

* * * * *

UNITED STATES PATENT AND TRADEMARK OFFICE
CERTIFICATE OF CORRECTION

PATENT NO. : 5,502,559
DATED : March 26, 1996
INVENTOR(S) : Ken R. POWELL et al.

It is certified that error appears in the above-indentified patent and that said Letters Patent is hereby corrected as shown below:

<u>Claim 19</u>:

Col. 16, Line 17, after "signals," delete "a logarithmic subtraction circuit that solves for $V_0$, a".

<u>Claim 21</u>:

Col. 16, Line 33, delete "portion".

Signed and Sealed this

Eleventh Day of June, 1996

*Attest:*

BRUCE LEHMAN

*Attesting Officer*     *Commissioner of Patents and Trademarks*